US00PP12450P2

(12) United States Plant Patent
Roberson

(10) Patent No.: US PP12,450 P2
(45) Date of Patent: Mar. 12, 2002

(54) *LANTANA CAMARA* PLANT NAMED 'ROBPATCOW'

(76) Inventor: Robert J. Roberson, 31706 E. Pink Hill Rd., Grain Valley, Jackson County, MO (US) 64029

( * ) Notice: Subject to any disclaimer, the term of this patent is extended or adjusted under 35 U.S.C. 154(b) by 0 days.

(21) Appl. No.: 09/526,500

(22) Filed: Mar. 15, 2000

(51) Int. Cl.[7] ..... A01H 5/00
(52) U.S. Cl. ..... Plt./227
(58) Field of Search ..... Plt./227

(56) References Cited

U.S. PATENT DOCUMENTS

PP10,156 P * 12/1997 Roberson ..... Plt./227
PP10,856 P * 4/1999 Covington ..... Plt./227
PP11,310 P * 3/2000 Kearley, Jr. ..... Plt./227

* cited by examiner

*Primary Examiner*—Bruce R. Campell
*Assistant Examiner*—Kent L. Bell
(74) *Attorney, Agent, or Firm*—Rothwell, Figg, Ernst & Manbeck

(57) ABSTRACT

This invention relates to a new and distinct *Lantana camara* cultivar which is outstanding because of its very compact growth habit, strong tendency to self branching, dramatic tri-colored, continuous bloom display, dense forest green leaves and tendency to set seed infrequently.

2 Drawing Sheets

SUMMARY OF THE INVENTION

This invention relates to a new and distinct *Lantana camara* cultivar which is outstanding because of its very compact growth habit, strong tendency to self branching, dramatic tri-colored, continuous bloom display, dense forest green leaves and tendency to set seed infrequently. The claimed *Lantana camara* plant was primarily selected for these characteristics. This selection was made from a specially designed Lantana hybridizing program with said hybrid cultivars being planted and grown in Grain Valley, Mo.

ORIGIN AND ASEXUAL REPRODUCTION

Asexual reproduction of this cultivar by tip cuttings was directed by me, such reproduction establishing that the plant does in fact maintain the characteristics described, in successive generations.

Vegetative tip cuttings were taken in January from the original "Mother" plant (produced from seed) and rooted and grown in a greenhouse. These were planted outside as a 2 inch plug size in USDA Zone 5 in the first week of May and grown and observed through September. This outdoor evaluation process was conducted for at least two or more summer growing seasons to observe descriptive characteristics.

It should be noted that the plant was initially selected from a Lantana planting being grown near Grain Valley, Mo. in a cultivated area and has since been reproduced by tip cuttings in the vicinity of Grain Valley, Mo. with the new and distinct characteristics stated herein, found to be stable and reproduce true to type in successive generations as before recited.

*Lantana camara* is native to the subtropics and tropical North and South America. They are woody ornamentals which are not usually winter hardy North of USDA horticulture Zone 9. The roughish leaves range from yellow-green to green to blue-green and the two basic growth forms are mounding and trailing (weeping). Bloom color usually include yellow, white, cream, pink, or orange.

The cultivar of *Lantana camara* 'Robpatcow' may further be described as having a number of distinctive characteristics which are enumerated in the succeeding specific description but broadly stated as comprising a very compact growth habit of only 8–12 inches in height and width in one season, a strong tendency to self branching, a tri-colored bloom display which transitions from yellow (PMS #108) to buff-gold (PMS #1235) and then to orange (PMS #1655), dense forest-green (PMS #343) leaves with blue overtones, and reduced tendency to set seed. The continuous color display begins blooming at 6–7 weeks after cutting are made, or four weeks after potting. Almost no pinching is needed due to this cultivar's tendency to self-branching.

I have chosen to identify this new cultivar as *Lantana camara* 'Robpatcow'. This cultivar is being marketed in the United States under the name of Patriot™ Cowboy.

BRIEF DESCRIPTION OF THE DRAWING

The accompanying photographs show as nearly true as it is reasonably possible to make the same, in color illustrations of this character, typical leaves and flowers of the new variety. The photographic drawings illustrate the flower form, the distinctive color transitions of the flowers, and the very compact growth habit.

DETAILED DESCRIPTION

Figure 1:
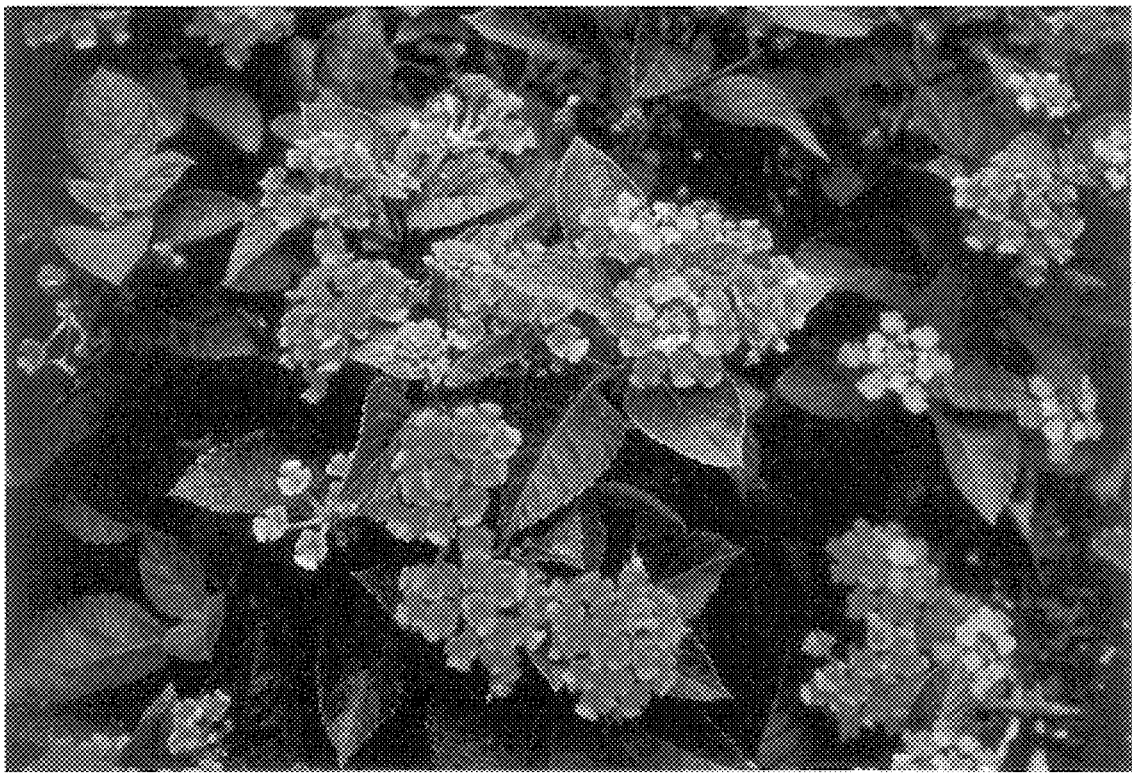
FIG. 1 illustrates the bloom cluster with varying maturity of the flowers (to display the color range as well as possible).
Figure 2:
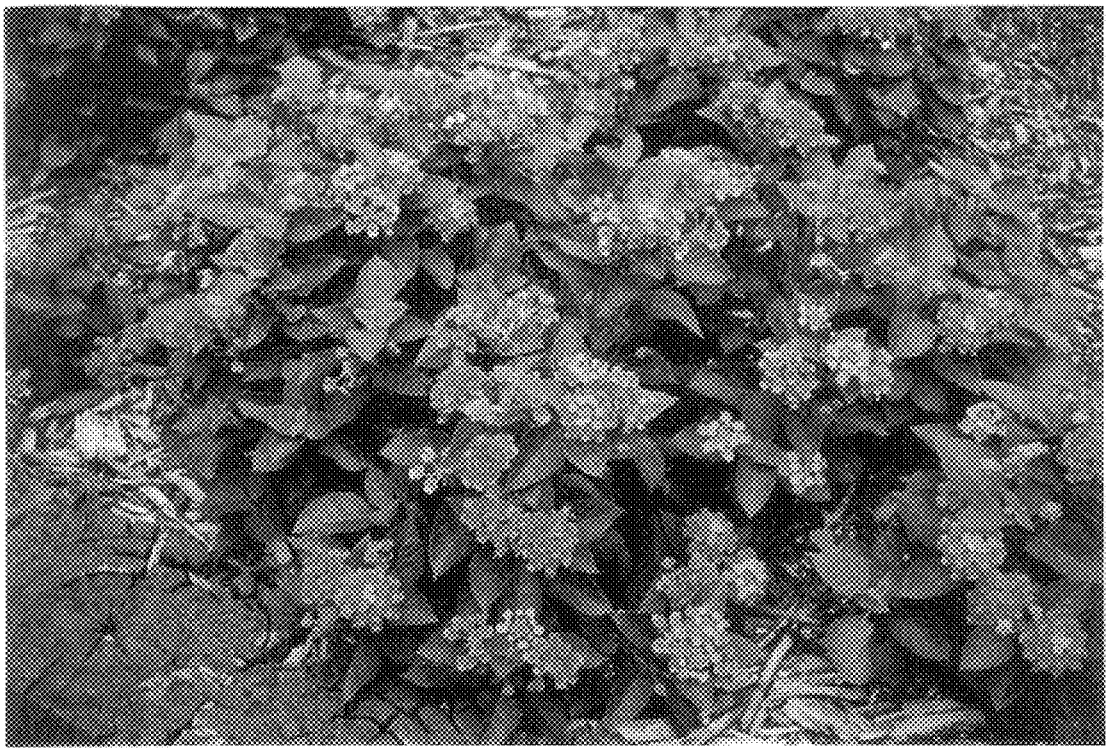
FIG. 2 illustrates the compact growth habit of the mature plant.

In order to more specifically identify the cultivar, descriptive details are set forth hereinafter, along with related aspects of the plant which serve to distinguish the same, all colors being noted as compared with the Pantone Matching System (PMS). The measurements and colors were recorded from mature 8 month old (from the time tip cuttings were taken) plants grown in the vicinity of Grain Valley, Mo.

Parentage:

*Seed parent.*—*Lantana camara* 'Robcomplan' (U.S. Plant Pat. No. 9,837) in a semi-controlled open pollination.

*Pollen parent.*—*Lantana camara* 'Robcomplan' (U.S. Plant Pat. No. 9,837).

Propagation: Asexual reproduction by tip cuttings started near Grain Valley, Mo.

Plant descriptions:

*Inflorescence and reproductive parts.*—The inflorescence is a flat topped round cluster of 25–30 flowers. The individual clusters are determinate and arise from the leaf axils. Each individual flower is slightly un-symmetrical with a bilateral symmetry and is subtended by a single bract. The bract has a length of ⅜"; width is 1/32" at the widest point; shape is lanceolate; apex is acute; base is truncate; margin is smooth with slight pubescence; color of both upper and lower surfaces is PMS #370 at the base blending to PMS #357 at the apex; lower surface has stronger pubescence. The perianth consist of: the Calyx (5 united sepals) and the Corolla (5 united petals with narrow tube). The flowers are zygomorphic, hermaphroditic, and have 4 introrse stamens which are didynamous. Single pistil which is usually vestigal and somewhat deformed. The ovary is superior, the style is terminal, and the stigma is lobed. The ovary is 2 locular, but is divided into 4 locules by a false septum in each locule. The placentation is axile with 2 ovules per carpel. The sepals, though not perceivable by the naked eye, when magnified can be observed and described as fused and comprising a short tubular calyx approximately 1/32" long. Slightly translucent in appearance, they have a coloration of PMS #370 on both surfaces. Petals have a fused corolla with fingerlike projections and have a length of ⅝" from base to tip; width of 5/16"; funnel shape; apex is irregular with 4–5 lobes; base is fused. Ultimate plant height is 12" when measured from the soil to the top of the inflorescence; ultimate plant diameter is 12". The fruit classification is drupe and potentially contains 2 seeds 3/16" in diameter. When fruit forms, it is green (PMS #363); then matures through a deep purple (PMS #533) to a near black (PMS #532).

*Inflorescence dimensions.*—Bloom cluster — 1.5" in diameter. Single Flower — 0.25". Pedicel length — 1.1"; color is green (PMS #370). Corolla tube — 0.375".

*Inflorescence colors.*—Buds — Cream (PMS #607); length is 1/16"; diameter is 1/32". The petals color at first opening — Upper surface is Bright yellow (PMS #108); lower surface is pale yellow (PMS #120); Transitions through to an upper surface of buff gold (PMS #1235); lower surface is cream-yellow (PMS #1205); Mature — Upper surface is Orange (PMS #1655); lower surface is pale gold-orange (PMS 1345). Transition Time — 24 hours (approximately). Tube — Exterior color is Salmon in all stages (PMS #170); interior color is pale yellow (PMS #127).

*Developmental pattern.*—First flowers develop in a circular pattern on the periphery of the inflorescence. The average plant grown outdoors for 6–8 months will typically produce 70–100 inflorescences at peak blooming. Lastingness of individual blooms: From early bud stage to the aborting of the last flower is typically 8–12 days.

*Leaves and stems.*—Leaf Shape: Ovate. Leaf Margins: Serrate. Leaf Tip: Acute. Leaf Base: Obtuse. Leaf Veins: Pinnate. Leaf Surface: Rough due to bristly hairs. Leaf Arrangement: Opposite. Leaf Color: Immature leaves — upper surface is forest green (PMS #349); lower surface is green (PMS #378) maturing to an upper surface color of blue green (PMS #343); lower surface color of green (PMS #378). Leaf Size: Length 2". Petiole Length is 0.5"; diameter is 1/16"; color is green (PMS #370). Width 1.25". Peduncle: Color is green (PMS #370); length is ⅞–1¼"; diameter is 1/16" at midpoint. Stem: Square in youth becoming round and woody with age; length is 6–8"; diameter is ⅛" at midpoint on the stem; internode length is ¼–1"; immature color is green (PMS #370) and mature color is (PMS #147).

Roots: Highly branched and fibrous.

Flowering time: The color display begins blooming at 6–7 weeks after cuttings are made, or 4 weeks after potting, and continue until temperatures drop below 45 degrees Fahrenheit.

Fragrance: The flowers have a medium to strong minty fragrance in the early yellow and buff gold stages and have little to no fragrance in the orange stage before aborting.

Diseases: No known diseases noted to date.

General observations: *Lantana camara* 'Robpatcow', with its dwarf and very compact growth habit is ideal for the smaller garden and landscape designs and the patio/pot culture trend. The lack of need to pinch for compact growth and the self-branching quality is a very time saving feature for the home gardener.

For the purpose of ornamental horticulture in our present living environments which include smaller yards and patio gardening, *Lantana camara* plant 'Robpatcow' is ideal due to several characteristics:

A. It is an excellent plant for mass planted ground covers, low borders, hanging baskets or floral short (12–15 inches) specimen standards. *Lantana camara* 'Robpatcow' will produce a continuous display of bright colors throughout the summer.

B. Self-branching is spontaneous, so almost no pinching is necessary. This growth habit, atypical in lantanas, produces a full compact display plant with little care or attention on the part of the gardener.

C. The leaves are smaller and more closely arranged than other lantanas, which enhances the "compact" display. It forms a compact mound 12"×12" in one season. Its very compact growth habit with small leaf size, short internode spacing and tendency toward self-branching places 'Robpatcow' in a category all its own, as this "compact habit" is not typical for any other lantana, other than the parent plant, that we are aware of.

D. *Lantana camara* 'Robpatcow' has a reduced tendency to set seed, therefore the inflorescence gives a longer display of color to the garden.

COMPARISON TO KNOWN VARIETIES

*Lantana camara* plant 'Robpatcow' should be compared with *Lantana camara* 'Robcomplan' (U.S. Plant Pat. No. 9,837) for its compact habit, growth rate, mature size, foliage color and shape. However, 'Robpatcow' is a new color in the compact Lantana plants. The only other compact Lantana plant that applicant is aware of is the patented parent, 'Robcomplan'.

The most distinguishing characteristic which differentiates 'Robpatcow' from, the parent, 'Robcomplan', is the bloom color. 'Robcomplan' transitions from yellow, to sienna and orange, then to fuscia pink and displays a bloom with a multi-color effect in appearance. Robpatcow's blooms transition from yellow, a very brief buff-gold, and then quickly mature to a bright orange giving the appearance of being bi-colored in mass rather than tri-colored.

I claim:

1. The new and distinct cultivar of *Lantana camara* plant substantially as illustrated and described.

* * * * *